United States Patent [19]

Opalek

[11] Patent Number: 5,405,332
[45] Date of Patent: Apr. 11, 1995

[54] SHIELD APPARATUS FOR SYRINGE NEEDLE

[76] Inventor: A. Allen Opalek, 1821 Tustin Ave., Philadelphia, Pa. 19152

[21] Appl. No.: 218,426
[22] Filed: Mar. 28, 1994
[51] Int. Cl.⁶ ............................................. A61M 5/00
[52] U.S. Cl. ................................. 604/192; 604/263
[58] Field of Search ............... 604/110, 187, 263, 192

[56] References Cited

U.S. PATENT DOCUMENTS

| | | | |
|---|---|---|---|
| 4,909,792 | 3/1990 | Norelli | 604/192 |
| 5,151,089 | 9/1992 | Kirk, III et al. | 604/192 |
| 5,232,454 | 8/1993 | Hollister | 604/263 X |
| 5,242,417 | 9/1993 | Paudler | 604/192 |
| 5,312,369 | 5/1994 | Arcusin et al. | 604/263 X |

Primary Examiner—John D. Yasko
Attorney, Agent, or Firm—H. Gordon Shields

[57] ABSTRACT

Hypodermic needle safety apparatus includes an embodiment having a shield which includes a longitudinal slot and a cover which rotates on the shield and an embodiment in which the shield must be moved axially, along the longitudinal axis of the syringe and needle, to allow the needle to be moved through a slot for use. The shield is then pivoted by thumb or finger movement so that the needle moves through the exposed slot to allow use of the syringe and the needle. The shield or cover moves through an arc of about 180 degrees so that the shield is away from the needle during the use of the needle and syringe. The shield is pivoted back downwardly to cover the needle and then the shield is again moved longitudinally or axially so that the bottom of the needle is away from the slot. The longitudinal or axial movement of the cover or shield requires a positive movement, and accordingly the shield may not be accidently or inadvertently pivoted away from the needle to expose the needle.

18 Claims, 4 Drawing Sheets

SHIELD APPARATUS FOR SYRINGE NEEDLE

BACKGROUND OF THE INVENTION

1. Field of the invention

This invention relates to syringe needles and, more particularly, to a protective shield that covers a syringe needle until moved away from the needle by a positive movement.

2. Description of the Prior Art

Hypodermic syringes have needles through which fluid material is transferred between the hypodermic syringe and a patient or recipient. In the ordinary course of handling the hypodermic syringe, inadvertent contact with a needle may result in a puncture wound to an individual or to the bending of the needle or perhaps the blunting of the needle tip.

A puncture wound may result in the inadvertent transfer of material from the syringe to the person punctured, and such transfer may have drastic injurious or harmful results. In any event, the inadvertent contact may result in the contamination of the needle and the requirement for a change of the needle.

In the past, different types of safety caps or shield apparatus has been suggested for protecting the needle until the hypodermic syringe is ready for use.

Hypodermic needles of the prior art typically include a cap which is appropriately secured to the syringe and which must be physically removed prior to the use of the syringe. The physical removal is accomplished by a longitudinal or axial pull on the cap until the cap is past the end of the needle. The cap is then moved to the side and discarded. It will be noted that the user moves generally parallel to the needle as the user grasps the cap. If a sideways movement of the cap is made too soon, the needle may be bent.

There are also shield elements which include an outer syringe cylinder which moves axially on the syringe to expose the needle. The shield cylinder is secured by a twist lock type mechanism. Such twist lock mechanism is typically not used with a syringe larger than about twelve milliliters because the twist lock mechanism is not strong enough to withstand axial hits on the tip of the shield.

The apparatus of the present invention also includes a smaller diameter than the syringe barrel and the apparatus is closely linked to the needle base. These features prevent the needle shield from being pushed over the syringe body and from exposing the needle.

Other types of guard elements or assemblies also have been suggested. For example, U.S. Pat. No. 3,658,061 (Hall) disclosed a needle guard which is secured to the base of a needle and which pivots away from the needle in order to use the needle.

U.S. Pat. No. 4,623,336 (Pedicano et al.) discloses a needle sheath which resemble a funnel with a cap. The syringe is inserted into the conical portion of the funnel, with the needle extending into the conical extension or cylindrical portion for protection. The apparatus is designed to be used only once, and after use the cap is placed over the funnel end and is locked in place so that the apparatus may not be used again.

U.S. Pat. No. 4,747,836 (Luther) discloses a needle guard which is rotatably mounted to the base of the needle. The guard includes a longitudinal slot extending on the cylinder, and the cylinder is in turn secured to a semicircular element axially aligned with the needle. The slot in the cylinder is rotated on the needle to allow the needle to be removed from the apparatus. After use, the apparatus is placed on the needle again, and the slot is rotated away from the needle so that the needle is essentially fully enclosed.

U.S. Pat. No. 4,820,277 (Norelli) discloses a pivoting safety cover which includes a pair jaw members that fold over the needle and which pivot away from the needle. The two jaw elements pivot about 180 degrees away from the needle to allow the needle, and the syringe, to be used.

U.S. Pat. No. 4,838,871 (Luther) is similar to the '836 (Luther) Patent discussed above.

U.S. Pat. No. 4,886,503 (Miller) discloses a pivoting needle guard which includes a rupturable plastic film closing one part of the guard. As the guard or cover pivots away from the needle, the plastic film ruptures to expose the needle and to allow the needle and syringe to be used.

U.S. Pat. No. 4,921,489 (Frizzell) discloses another shield for a hypodermic needle which includes a pair of flat members which are hinged to a plate. The flat members are hinged to the plate and they move from a retracted position adjacent to a central sheath to an open position in which they provide a shield for the fingers of the user of the apparatus. The sheath also pivots away from the needle to allow the syringe and needle to be used.

U.S. Pat. No. 4,944,397 (Miller) discloses another type of sheath apparatus for hypodermic needle in which the sheath pivots relative to the needle. The sheath comprises a covering with a relatively opening in the covering. The covering is closed by a manually strippable tape. The tape is removed prior to the use of the needle, and the cover is then pivoted away from the needle for use.

U.S. Pat. No. 4,944,731 (Cole) disclosed another type of shield apparatus which uses a pair of pivoting elements secured to the base of the syringe. The pivoting elements move outwardly from each other to allow use of the syringe. The pivoting elements pivot through about 180 degrees so they are disposed alongside the barrel of the syringe.

U.S. Pat. No. 4,950,249 (Jagger et al.) discloses another type of hypodermic needle apparatus in which there are a pair of elements that are pivotally secured to the base of the syringe. There is a hub ring or a ring hub, and the pivoting elements are molded as part of the hub in their open position. Accordingly, when the sheath elements are pivoted to the closed position, there is an inherent bias in the material to urge the sheath elements to their open position. When the sheath is open, the elements move outwardly or pivot outwardly substantially 90 degrees to allow use of the syringe apparatus.

U.S. Pat. No. 5,139,489 (Hollister) discloses a needle protective cap which pivots on a living hinge relative to a bottom element. Hollister's U.S. Pat. No. 5,154,285 discloses similar apparatus.

U.S. Pat. No. 5,151,089 (Kirk et al) discloses a protective sheath for a syringe that pivots relative to a support base which is secured to the syringe assembly.

The apparatus of the present invention differs from the prior art in its structure. While there are elements of the prior art, as discussed above, that include only a single element, most of them utilize a pair of elements which move in a clam shell type pivoting arrangement from the closed position in which they form a shield for a needle to their open position for use of the syringe and needle. The apparatus of the present invention includes several embodiments which include only a single pivoting element. In practically all cases, there is a guard element which moves about a sheath element for covering and uncovering a slit in the sheath element through which the needle may pass. The pivoting action of the shield apparatus of the present invention is different from the prior art elements and accordingly provides a positive lock in the open position in several embodiments.

It will be noted that while the drawing figures and the specification refer primarily to needles of hypodermic syringes, the apparatus of the present invention applies to all instruments in which a needle is attached to a fluid element for the transfer of liquid material, such as vacutainers, cannulae, and the like.

Moreover, the shield apparatus of the present invention is primarily a needle guard, or is primarily associated with a needle rather than with the syringe, per se. In the circumstances where a needle and syringe are prejoined by a manufacturer, the apparatus is naturally associated with both.

SUMMARY OF THE INVENTION

The invention described and claimed herein comprises shield apparatus for a syringe in which the shield apparatus moves longitudinally or axially along a syringe in response to positive movement of the user, and the apparatus then pivots away from the needle to expose the needle for use. In some embodiments, the shield apparatus pivots through an arc of about 180 degrees so that the hand of the user which moves the shield from the needle remains away from the needle at all times. The pivoting of the shield is accomplished by movement of a user's thumb or by fingers. In another embodiment the shield moves axially along the syringe barrel before pivoting.

Among the objects of the present invention are the following:

To provide new and useful shield apparatus for the needle of hypodermic syringes, vacutainers, cannulae, and the like;

To provide new and useful pivoting shield apparatus for the needle of a hypodermic syringe;

To provide new and useful cover apparatus for a needle in which a longitudinal or axial movement of the cover takes place prior to the pivoting of the cover to allow use of the needle and syringe;

To provide new and useful needle shield apparatus in which a needle shield may rotate relative to a needle;

To provide new and useful safety cover apparatus for the needle of a hypodermic syringe in which the cover is movable longitudinally relative to the syringe; and To provide new and useful safety shield apparatus for the needle of a syringe in which a shield is pivoted by thumb or finger action through an arc of about 180 degrees from its shield position to a position wherein the syringe and needle may be used.

DESCRIPTION OF THE PREFERRED EMBODIMENT

Figures 1, 2, 3, 4, 5, 6, 7, 8:
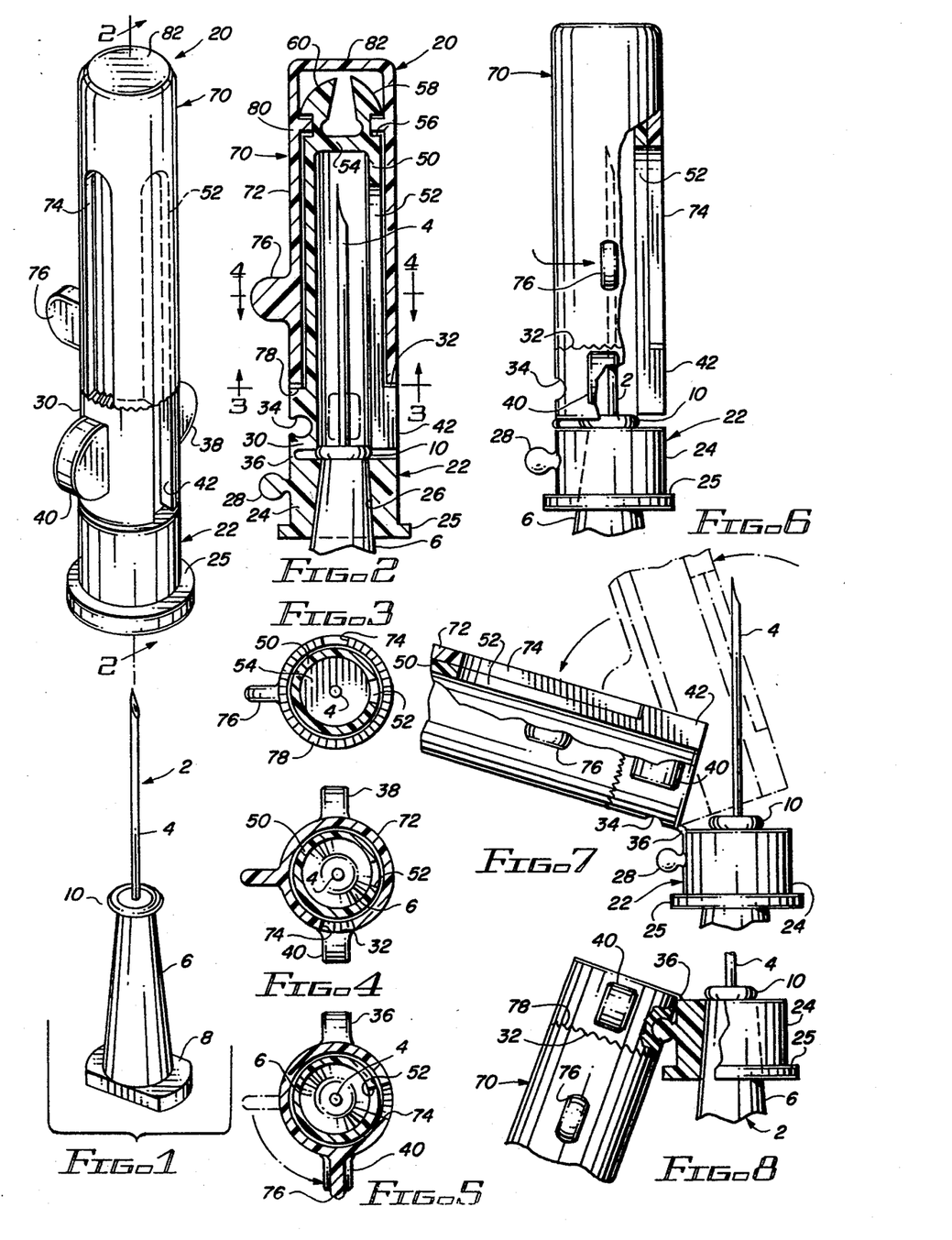
FIG. 1 is an exploded perspective view of the apparatus of the present invention.
FIG. 2 is a view in partial section taken generally along line 2—2 of FIG. 1.
FIG. 3 is a view in partial section taken generally along line 3—3 of FIG. 2.
FIG. 4 is a view in partial section taken generally long line 4—4 of FIG. 2.
FIG. 5 is a view in partial section taken sequentially following FIG. 4 and illustrating the operation of the apparatus of the present invention.
FIG. 6 is a side view partially broken away illustrating the operation of the apparatus of the present invention.
FIG. 7 is a side view, partially broken away, sequentially following FIG. 6 in illustrating the operation of the apparatus of the present invention.
FIG. 8 is a side view sequentially following FIG. 7 in illustrating the operation of the apparatus of the present invention.

FIG. 1 is an exploded perspective view of needle safety shield apparatus 20 embodying the present invention. The apparatus 20 is spaced apart from a syringe needle assembly 2, which includes a needle 4, a needle holder 6, and an outwardly extending flange 8 which may be used to secure the needle assembly 2 to a syringe (not shown). For example, the flange 2 may extend into the threaded luer connection on a syringe.

At the top of the needle holder 6, which has a tapering, generally conical configuration, there is an outwardly extending ridge 10. The ridge 10 is circumferentially extending and serves to help hold the apparatus 20 in place.

The needle safety shield apparatus includes a base ring 22 which is disposed about the needle holder 6. The base ring 22 is disposed on to the needle holder 6 adjacent to the needle 4. The base ring 22 remains on the needle holder 6 during the use of the apparatus 20 and of the assembly 2 as assembled to a syringe. The base ring 22 may rotate on the needle holder, as will be discussed below.

There is an outwardly extending flange 25 on the base ring 24 which may serve to help install the safety shield apparatus 20 to the needle assembly 2, to reinforce the base ring 24, and to help orient the base 22 relative to the needle 4, as required.

FIG. 2 is a view in partial section of the shield assembly 20 disposed on the needle holder 6, with the needle 4 extending upwardly into the shield assembly 20. FIGS. 3, 4, and 5 are views in partial section illustrating the construction and the sequential operation of the shield assembly 20. FIGS. 3 and 4 are taken generally along lines 3 and 4 of FIG. 2, while FIG. 5 is generally the same view and FIG. 4, but illustrating the operation of a portion of the shield assembly 20.

FIG. 6 is a side view of the shield assembly 20 on the needle holder 6, and essentially comprises a side view, with portions broken away, which corresponds to FIG. 5 in the illustration in the operation of the shield assembly 20. FIGS. 7 and 8 are side views sequentially illustrating the operation of the shield assembly 20. FIGS. 6 and 7 correspond to FIG. 6 in the operation of the shield assembly 20.

For the following discussion, reference will be made to all of the FIGS. 1-8, and as necessary, attention will be drawn to a particular figure.

The base 22 of the shield assembly 20 includes a cylindrical lower portion 24. The cylindrical lower portion 24 includes the bottom flange or rim 25 which extends outwardly from the cylindrical portion 24. As indicated above, the outwardly extending flange helps to install the shield assembly 20 on the needle holder 20 and in particular helps in moving the base 22 over the ridge 10 of the needle holder 6.

Within the cylindrical portion 24 is a bore 26. The bore 26 has a generally conical configuration to match the tapering conical exterior configuration of the needle holder 6.

Extending outwardly from the cylindrical portion 24 is a locking pin 28. The locking pin 28 will be discussed in detail below.

The shield assembly 20 also includes a cylindrical shield portion 30 which is pivotally secured to the base 22 by a hinge 36. Extending into the cylindrical portion 30 is a locking slot or recess 34 that cooperates with the locking pin 28 to lock the cylindrical portion 30, and the other elements secured thereto, to the base 22 when the shield assembly has been displaced in order for the syringe, in particularly the needle 4 of the syringe, to be used as is appropriate.

Extending outwardly from the cylindrical portion 30 are a pair of pivot tabs 38 and 40. The pivot tabs 38 and 40 will be discussed in more detail particularly in conjunction with FIGS. 7 and 8. A vertically or axially extending slot 42 extends through the cylindrical portion 30. The needle 4 moves through the slot 42, as will be discussed below, and is best shown in FIGS. 7 and 8.

Extending upwardly from the cylindrical portion 24 of the base 22 is an upper cylindrical needle shield 50. The upper cylindrical needle shield 50 includes a vertical slot 52 which is appropriately aligned with the slot 42 in the base 30. A shoulder 32 is defined at the juncture of the upper needle shield 50 and the cylinder 30. The shoulder 32 extends outwardly relative to the needle shield 50. The shoulder 32 includes a plurality of serrations which are in the nature of ratchet serrations, which will be discussed below.

The upper needle shield includes the top wall 54. A circumferentially extending groove 56 is located above the top wall 54. A pair of top ears 58 extend upwardly from the top wall 54 and above the groove 56. The top ears have sloping cam surfaces 60 on them for purposes of helping to install an outer cylindrical cover 70 on the cylindrical portion 30 of the shield assembly 20.

The outer cylindrical cover 70 includes a lower cylindrical portion 72, the inside diameter of which is slightly greater than the outside diameter of the upper needle shield 50. A vertically or axially extending slot 74 extends through the cylindrical portion 72. Extending outwardly on the cylindrical portion 72, and located about 90 degrees from the vertical slot 74 is a tab 76. The tab 76 is used to rotate the outer cylindrical cover 70 relative to the needle shield 50.

The bottom of the cylindrical portion 72 of the cover 70 comprises a plurality of serrations 78 which matingly engage the serrations 32 of the cylindrical portion 30 of the shield assembly 20. The mating serrations 32 and 78 engage each other in a ratchet type engagement which allows the cover 70 to move only in one direction relative to the needle shield 50 and to the shield lower cylindrical portion 30 and, accordingly, of the base 22. The base 22 may rotate under a certain, predetermined force or tension so as to be unobstructive to the needle and to permit proper needle alignment relative to the shield apparatus 20.

The cover 70 is closed by a top wall 82. Spaced apart downwardly from the top wall 82, there is a flange 80 which extends inwardly from the cylindrical portion 72. The flange 80 extends into the groove 56 of the needle shield 50.

It will be understood that the cam surfaces 60 of the ears 58 help to move the flange 80 into the groove 56. The ears 58 are relatively movable in that they will bend or deform to the center of the cover 70 as the flange 80 is cammed downwardly over the ears 58. Accordingly, the cover 70 is moved downwardly in place over the upper needle shield 50.

As may be best understood from FIGS. 3 and 4, when the outer cylindrical cover 70 is in place on the upper needle shield 50, the slot 52 in the needle shield 50 and the slot 74 in the cylindrical cover 70 are not aligned. Rather, the slot 74 is preferably about 90 degrees away from the aligned slots 42 and 52 so that the needle 4 is protected from inadvertent contact.

Again, as best shown in FIG. 4, the tab 76 is about 90 degrees from the pivot tabs 38 and 40. However, when the use of the syringe to which the needle assembly 2 and the shield assembly 20 are secured is desired, the outer cylindrical cover 70 is pivoted counterclockwise, as indicated in FIG. 5, by movement of the tab 76. When the tab 76 is aligned with the tab 40, the vertical slot 74 is appropriately aligned with the slot 52 and with the slot 42.

FIG. 6 shows the alignment of the various elements, ready to pivot the upper portion of the shield assembly 20, which includes the middle cylindrical portion 30, the upper needle shield 50, and the outer cylindrical cover 70, relative to the base 22.

With the various elements aligned, as shown in FIGS. 5 and 6, the pivot tabs 38 and 40 may be used to pivot the shield portions 30, 50, and 70 relative to the base 22. This is shown in FIG. 7. The needle 4 moves through the aligned slots 42, 52, and 74 so that the needle 4 is bared for its intended use.

To lock the needle shield 50 and the outer cylindrical cover 70 in place relative to the base 22, the locking pin 28 extends into the locking slot 34. This is best shown in FIG. 8. The locking slot or recess 34 receives the locking pin 28 and the shield assembly 20 is then maintained in its desired orientation relative to the needle 4 while the appropriate use of the needle 4, and the syringe to which it is secured, is used as intended.

To secure the cylindrical portion 30, with its locking slot recess 34, to the base 22, pressure is applied against the pivot tabs 38 and 40. The upper needle shield 50 and outer cylindrical cover 70, as secured to the cylindrical portion 30, pivot relative to the base 24 on the living hinge 36 until contact is made between the pin 28 and the slot or recess 34. Continued pressure on the pivot tabs causes the engagement of the pin 28 and the recess or slot 34 until a locking engagement occurs.

The cylindrical portion 30, with the needle shield 50 and the cover 70 will remain as illustrated in FIG. 8 during the use of the particular apparatus to which the needle assembly 2 and the shield assembly 20 are secured to accomplish the desired fluid transfer.

It will be noted that the base 22, disposed on the needle holder 6, prevents the shield apparatus 20 from being pushed axially past the tip of the needle 2. Moreover, the diameter of the shield apparatus 20 prevents it from being axially over the syringe body to expose the needle tip.

Figures 9, 10, 11, 12, 13:
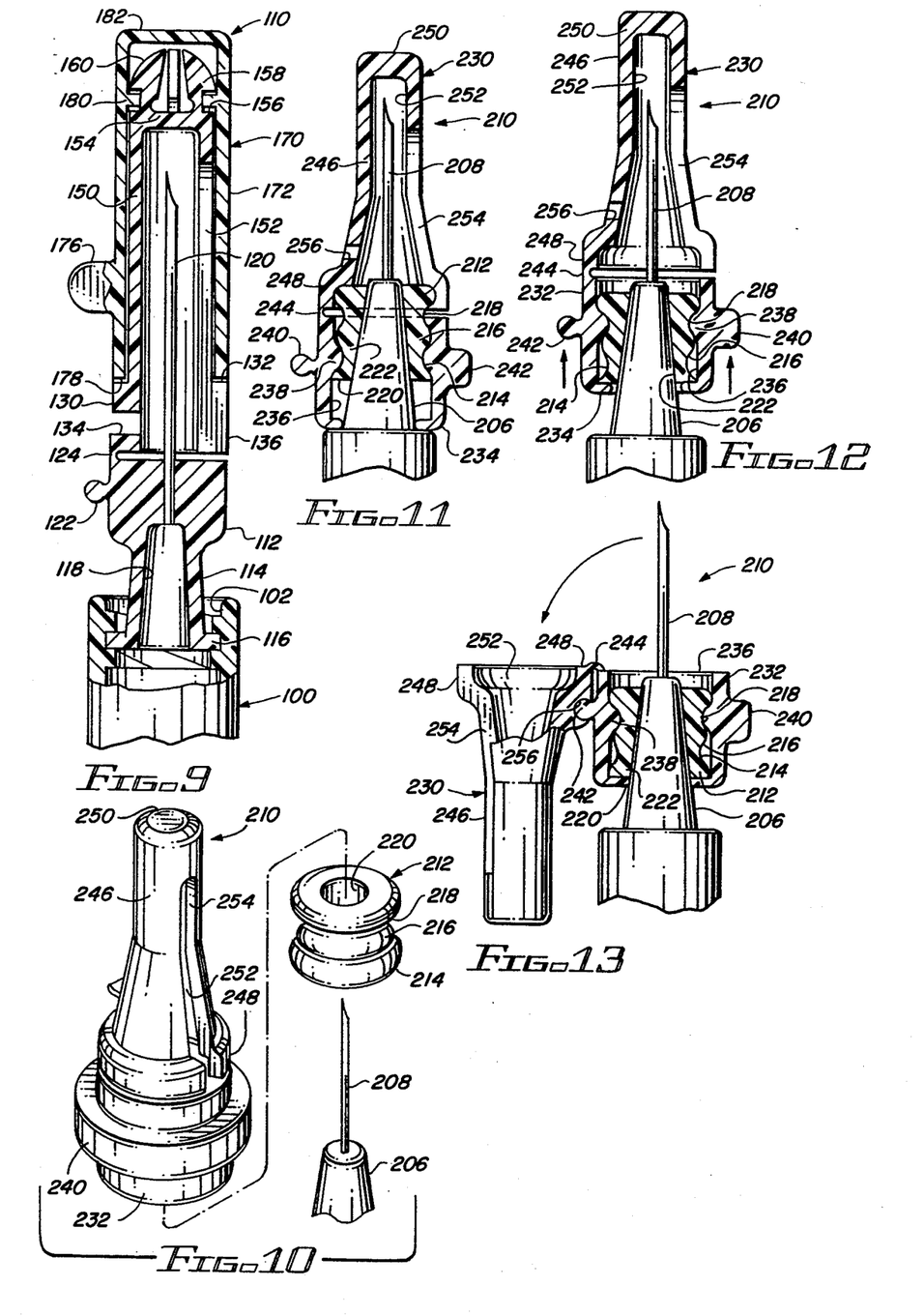
FIG. 9 is a view in partial section of an alternate embodiment of the apparatus of the present invention.
FIG. 10 is an exploded perspective view of another alternate embodiment of the apparatus of the present invention.
FIG. 11 is a view in partial section of the apparatus of FIG. 10.
FIG. 12 is a view in partial section illustrating the operation of the apparatus of FIGS. 10 and 11.
FIG. 13 is a view in partial section sequentially following FIG. 12 illustrating the operation of the apparatus of FIGS. 10 and 11.

An alternate embodiment of the needle assembly 2 and the shield assembly 20 is illustrated in FIG. 9. FIG. 9 is a view in partial section of a "standard" hypodermic syringe 100 with an integral needle and shield assembly 110 secured thereto. It will be noted that while the various embodiments illustrated show integral needles, the apparatus of the present invention works just as well when a needle assembly is attached to a syringe by the end user. Moreover, even in an integral unit the base may be free to rotate in a circular groove rather than in a threaded groove arrangement as illustrated.

The hypodermic syringe 100 is a generally standard or conventional syringe, with a luer groove 102 at the end of the syringe for connecting the syringe 100 to a standard or typical needle assembly such as shown in FIG. 1. However, in the embodiment of FIG. 9, an integral needle shield apparatus 110 is secured to the hypodermic syringe 100.

The integral needle shield apparatus 110 includes a lower base 112, and an upper base 130 is hingedly secured to the lower base 112. An outer cylindrical cover 170 is in turn secured to the upper base 130.

The lower base 112 includes a lower connecter portion 114 which terminates in an outwardly extending connector flange 116. The connector flange 116 extends into the luer threads, or grooves or channels, 102 to allow for rotation of the base 112 relative to the syringe 100. An inner bore 118 extends through the connector portion 114. A needle 120 is in turn secured within the fixed base 112 and extends upwardly therethrough. The bore 118 appropriately communicates with the base of the needle 120.

A locking pin 122 extends outwardly from the base 112. A hinge 124, which is essentially a living hinge, connects the fixed base 112 to the upper base 130.

The upper base 130 includes a serrated shoulder 132, and the serrated shoulder 132 is substantially identical to the serrated shoulder 32 of the cylindrical portion 30 of the shield assembly 20, discussed above.

A locking slot or recess 134 extends through the upper base 130, or into the upper base 130, for receiving the locking pin 122 to secure the upper base 130 and the needle shield 150 and the cylindrical cover 170 to the lower base 112, substantially the same as discussed above for the shield assembly 20.

A needle slot 136 extends through the upper base 130. The needle shield is a cylindrical element which extends upwardly from the upper base 130. The serrated shoulder 132 is disposed between the needle shield 150 and the upper base 130. The shoulder 132 extends radially outwardly from the needle shield 150.

The needle shield 150 includes a vertical slot 152 which comprises a continuation of the needle slot 136. The needle 120 extends through the aligned or continuation slots 136 and 152 when the upper base 130, with its needle shield 150 and the cover 170 pivot relative to the lower base 112.

Also secured to the upper base 130, which comprises a generally cylindrical portion of the apparatus 110, are two pivot tabs, not shown. The pivot tabs extend radially outwardly from the upper base 130 substantially identically to the pivot tabs 38 and 40 in regard to the cylindrical portion 30 of the shield assembly 20, all as discussed above. The pivot tabs extending outwardly from the upper base 130 functions substantially the same as do the pivot tabs 38 and 40.

The needle shield 150 extends upwardly from the upper base 130. The needle shield 150 is generally cylindrical in configuration with an interior bore into which the needle 120 extends. A needle slot 152 is aligned with the slot 136 in the base 130. The needle 120 extends through the aligned slots 136 and 152 as the needle shield 150 and the outer cylindrical cover 170 pivot to expose the needle 120.

The needle shield 150 is closed by a top wall 154. A pair of top ears 158 extend upwardly from the top wall 154. A radially inwardly and circumferentially extending groove 156 extends through the base of the top ears 158 and the top wall 154. The groove 156 is substantially the same as the groove 56 of the needle shield 50. Likewise, the ears 158 are substantially identical to the ears 58 of the shield 50. The top ears 158 include cam surfaces 160, which also are substantially identical in configuration and purpose to the cam surfaces 60 of the top ear 58.

The outer cylindrical cover 170 is disposed about the needle shield 150. The outer cylindrical cover 170 includes a cylindrical portion 172 through which extends a vertical slot. The vertical slot is not shown in FIG. 9. A rotation tab 176 extends outwardly from the cylindrical portion 172. The bottom of the cylindrical portion 172 includes ratchet serrations 178 which matingly engage the ratchet serrations on the shoulder 132 of the upper base 130.

The cylindrical portion 172 is closed by a top wall 182. The radially inwardly extending flange 180 is spaced apart from the top wall 182 and extends into the groove 156 of the needle shield 150. The various elements correspond substantially identically to the various elements of the cover 70 discussed above in conjunction with the shield apparatus 20. Again, the outer cylindrical cover 170 is secured to the needle shield 150 for relative rotation in one direction only through the mating ratchet serrations 132 and 178 on the upper base 130 and the cylindrical cover 170, respectively.

The outer cylindrical cover 170 is rotated relative to the needle shield 150 through the rotation tab 176 until a vertical slot (not shown) in the cover 170 is aligned with the slots 136 and 152. At this point, pressure against pivot tabs (not shown) on the upper base 130 causes the upper base, with the needle shield 150 in the outer cylindrical cover 170 as secured thereto, to pivot on the hinge 124 relative to the lower base 112. The needle 120 moves through the aligned slots and the needle is then available for use.

The locking slot or recess 134 and the upper base 130 receives the locking pin 122 in the lower base 112 to appropriately secure the upper base 130 and its assembled elements to the lower base 112, as desired. Essentially, the operation of the various elements is substantially the same as that discussed above for the shield apparatus 20. The primary difference, of course, is that the needle shield apparatus 110 is integral, and it accordingly is secured directly to the syringe 100.

Note that the apparatus 110 provides essentially double protection for the needle 120. There are, effectively, two shields, an inner shield 150 and an outer shield 170.

FIG. 10 is an exploded perspective view of an alternate embodiment 210 of the apparatus of the present invention. The apparatus 210 is shown spaced apart from a hypodermic needle holder 206 and a needle 208 which extends outwardly from the needle holder 206.

FIG. 11 is a view in partial section through the shield apparatus 210, with the shield apparatus 210 secured to the needle holder 206 and covering the needle 208. In FIG. 11, the needle shield is in its closed, safe, position, shielding the needle 208. FIG. 12 is a view in partial section sequentially following FIG. 11. FIG. 13 is also a view in partial section and it is sequentially following FIG. 12. FIGS. 11, 12, and 13, illustrate the use or function of the apparatus 210 with respect to the hypodermic needle 208. For the following discussion, reference will be made to FIGS. 10, 11, 12, and 13.

The alternate embodiment 210 includes an inner base element 212 which is appropriately secured to the needle holder 206 and which may rotate relative thereto. The inner base 212 includes two grooves, a bottom groove 214, and a top groove 218. A ridge 216 is disposed between the two grooves 214 and 218. The base 212 also includes a generally flat or planar bottom 220. The inner base 212 also includes a central bore 222. The configuration of the central bore 222 is substantially the same as the exterior configuration of the needle holder 206.

A shield assembly 230 is movable on the inner base 212. The shield assembly 230 includes an outer base 232 which matingly engages the inner base 212 and is movable on the inner base 212. The outer base 232 includes an inwardly extending bottom flange 234. The bottom flange 234 acts as a stop element against the bottom 220 of the inner base 212.

Within the outer base 232, and extending upwardly from the bottom flange 234, is a bore 236. A ridge 238 extends inwardly from the bore 236. The ridge 238 is relatively smoothly configured, and it matingly engages the grooves 214 and 218 of the fixed base 212. When the shield apparatus 210 is in its closed, or safe, position, as shown in FIG. 11, the ridge 238 is disposed in the bottom groove 214. When the shield apparatus 210 is moved from the safe or closed position shown in FIG. 11 to the position illustrated in FIG. 12, the shield 230 is moved upwardly relative to the fixed base 212 such that the ridge 238 is disposed in the top groove 218.

A rim 240 extends outwardly from the base 232. The primary purpose of the rim 240 is to move the shield 230 relative to the fixed base 212. The movement is, as is discussed above, vertically upwardly and downwardly.

A locking pin 242 comprises a portion of the rim 240. The purpose of the locking pin 242 will be discussed in detail below, and is best shown in FIG. 13.

A cap 246 is secured to the base 232 by a living hinge 244. The cap 236 effectively covers the needle 208 until it has been moved away, as shown in FIG. 13.

The cap 246 includes a bottom portion 248, to which the hinge is secured. That is, the living hinge 244 is essentially a joining element, and is integral with, both the bottom portion 248 of the cap 246 and the base 232.

The cap 236 is closed by a top wall 250. Within the cap 246 is an inner bore 252. The inner bore 252 receives the needle 208.

A slot 254 extends through the cap 246, including through the bottom portion 248. When the shield 230 is moved to its upper position, as shown in FIGS. 12 and 13, the slot 254 is in position to move relative to the needle 208. The cap 230 is accordingly in position to be pivoted on the hinge 244 relative to the base 232 and also relative to the base 212. The movement of the cap 230 is illustrated by the large arrow in FIG. 13.

A locking aperture or recess 256 extends through the cap 246 and receives the locking pin 242 of the base 232 to secure the cap 230 in the fixed position relative to the needle 208 and to the bases 212 and 232. The cap 246 is accordingly held away from the needle 208 to allow the needle 208, and the hypodermic syringe to which the needle 208 is secured, to be used.

After the hypodermic syringe and the needle 208 have been used, the cap 246 may then be pivoted on the hinge 244 relative to the two bases 212 and 232. When the cap 246 has been returned to the position shown in FIG. 12, with the needle 208 in the bore 252, the shield 230 may then be moved downwardly relative to the fixed base 212, or in the direction opposite to that indicated by the large arrows in FIG. 12, and to the position shown in FIG. 11. The ridge 238 of the base 232 is then moved from the top groove 218 of the base 212 to the bottom groove 214, as shown in FIG. 11. The shield apparatus 210 is then in a safe position relative to the needle 208. As illustrated in FIG. 11, the top of the slot 254 is below the end of the needle 208. Accordingly, the cap 246 cannot be pivoted relative to the needle 208, and the needle 208 is accordingly appropriately shielded.

As is perhaps best shown in FIG. 10, the outer diameter of the middle ridge 216 is slightly less than the outer diameter of those portions of the base 12 both below the bottom groove 214 and the top groove 218. This prevents the inadvertent movement of the shield 230 base 212.

In other words, while the flange 234 acts as a stop element for the shield 230 by its contact with the bottom 220 of the fixed base 212 when the shield 230 is moved to the upper position illustrated in FIG. 12, the fact that the diameter of the base 212 above the groove 218 also acts as a stop element to prevent the inadvertent upward movement of the shield 230 relative to the base 212. Moreover, the relatively larger diameter of the base 212 below the bottom groove 214 acts as a stop element to prevent the shield 230 from being moved downwardly so as to allow the tip of the needle 208 to contact the top wall 250 of the cap 246.

This downward movement of the shield 230, and particularly of the cap 246, is prevented by the configuration of the bottom portion 248 of the cap 246. That is, the configuration of the inner bore 252 is tapering so that contact is made between the cap 246 and the upper portion of the base 212 to limit the downward movement of the shield 230 relative to the base 212. This is best shown in FIG. 11.

It will be noted that the outer cylindrical cover 70, from the apparatus 20 of FIGS. 1-8, may also be used, if desired, with the apparatus 210 of FIGS. 10-13.

In the embodiments of FIGS. 9-13, it will be noted that the shield assemblies 110 and 210 are prevented from moving axially by the needle holder elements, such as the fixed base 112 and its associated elements, and the needle holder 206, respectively. Also, the relatively small diameter of the shields prevents them from being pushed axially over the syringe body to expose the needle tips.

A somewhat simpler and perhaps universal needle safety apparatus is illustrated in FIGS. 14-23. The apparatus of FIGS. 14-23 disclose apparatus that is designed primarily for use in restrictive area injections, such as in dental work. In such areas, an obstructive sheath or shield may be a hindrance and needs to be moved or shifted away. Moreover, there are situations where the operator desires to have the shielding mechanism displaced away from the needle part. Furthermore, there are various diameters of needle holders and syringes, and a flexible syringe hugging element may be desirable in order to allow a single shield design to be employed with the various sizes or diameters.

In some work, where standards in either plastic or steel are the general rule, the needles incorporate a uniform syringe hugging collar may be used. In other work, where standards are not employed, a flexible sized collar is needed. The apparatus of FIGS. 14-23 may be used in such situations.

Figures 14, 15, 16, 17, 18, 19, 20, 21, 22, 23, 24:
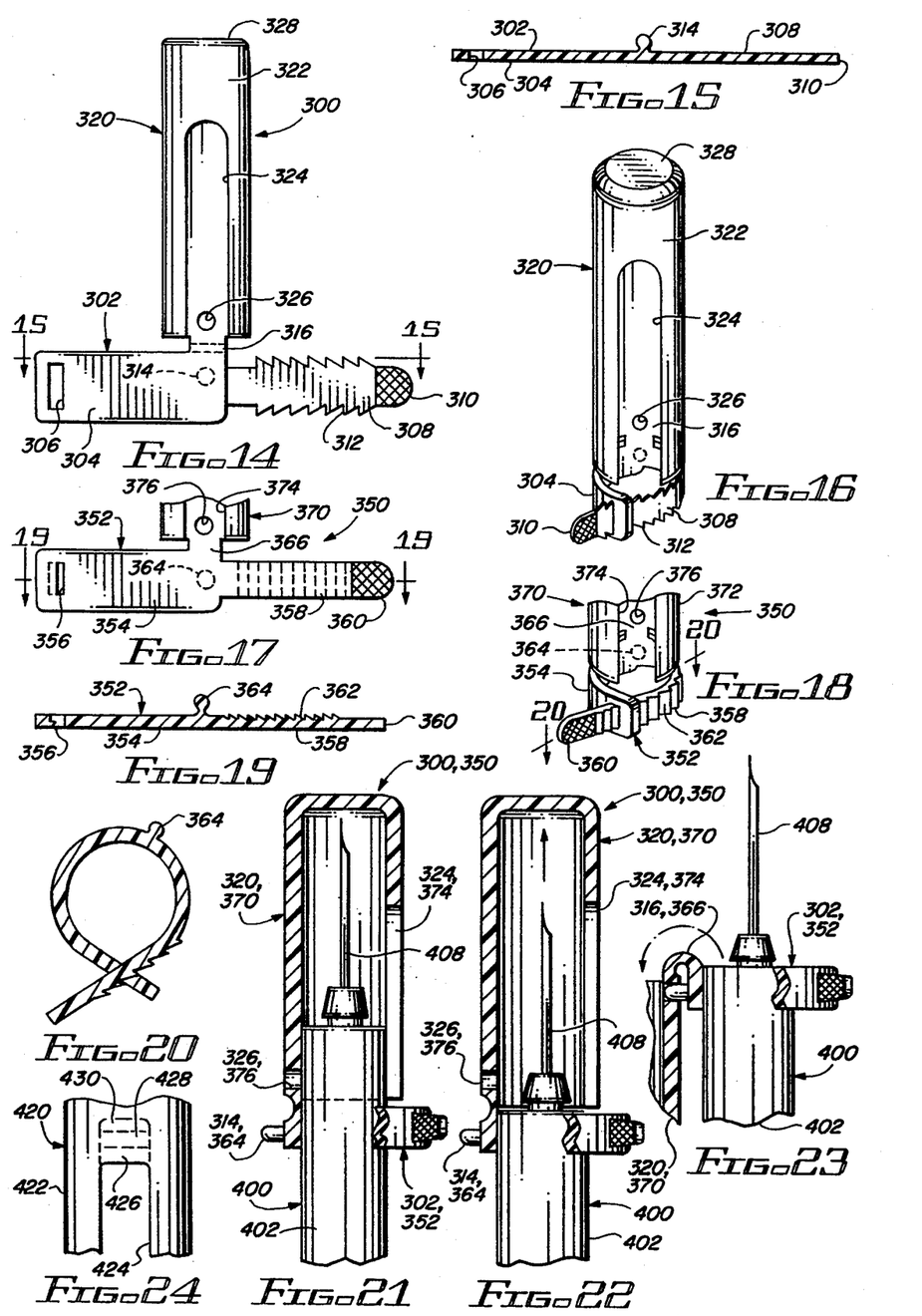
FIG. 14 is a plan view of another alternate embodiment of the apparatus of the present invention.
FIG. 15 is a view in partial section taken generally along line 15—15 of FIG. 14.
FIG. 16 is a perspective view of the apparatus of FIG. 14.
FIG. 17 is a plan view of a portion of the apparatus of FIGS. 14 and 16.
FIG. 18 is a perspective view of an alternate embodiment of a portion of the apparatus of FIGS. 14 and 16.
FIG. 19 is a view in partial section taken generally along line 19—19 of FIG. 17.
FIG. 20 is a view on partial section taken generally along line 20—20 of FIG. 18.
FIG. 21 is a side view illustrating the operation of the apparatus of FIGS. 14 and 16.
FIG. 22 is a side view showing sequentially the operation of the apparatus of FIG. 21.
FIG. 23 is a side view showing sequentially the operation of the apparatus of FIG. 22.
FIG. 24 is a side view of an alternate embodiment of a portion of the apparatus of the present invention.

For convenience, needles are not shown in FIGS. 14, 16, and 18, but it will be understood that the shield apparatus is used in conjunction with a needle, and that the shield apparatus is associated with the needles at the manufacturing location and not at the end user location. That is, the end user does not install the shield apparatus on the needle. Thus the showing of FIGS. 14, 16, and 18 is merely illustrative of the manufacturing or design perspective.

Needle shield apparatus 300, which comprises another alternate embodiment of the apparatus of the present invention, is illustrated in FIGS. 14, 15, 16, 17, 18, 19, and 20.

FIG. 14 is a side elevational view of shield apparatus 300, which comprises another alternate embodiment of the apparatus of the present invention. The shield apparatus 300 is, or may be considered as, a generic type shield apparatus which may be rather quickly or easily secured to virtually any type of hypodermic needle.

FIG. 15 is a view in partial section taken generally along lines 15—15 of FIG. 14 and showing a portion of the shield apparatus 300. FIG. 16 is a perspective view of the shield apparatus 300 in its use configuration. FIG. 17 is a plan view of an alternate embodiment of a portion of the shield apparatus 300. FIG. 18 is a perspective view of the elements shown in FIG. 17 in a use configuration. FIGS. 19 and 20 are views in partial section of the elements shown in FIGS. 17 and 18, respectively, taken generally along the lines 19—19 and 20—20, respectively.

For the following discussion, reference will be made to all of the FIGS. 14, 15, 16, 17, 18, 19, and 20. Specific reference to some of the figures will also be made in conjunction with details of the shield apparatus 300, and the alternate embodiments, as appropriate.

The hypodermic needle shield apparatus 300 includes a base 302 and a cap 320. The base 302 includes a strap portion 304 and a locking portion 308. An aperture 306 extends through the strap portion 304 towards one end of the strap portion, remote from the locking portion 308. The locking portion 308 includes an end 310, remote from the strap portion 304. The locking portion 308 includes a plurality of edge serrations 312 which extend outwardly from the top and bottom edges from the locking portion 308. The edge serrations 312 are disposed between the end 310 and the strap portion 304.

The locking pin 314 extends outwardly from the strap portion 304. The locking pin 314 is quite similar, if not substantially identical, to the locking pins discussed above in conjunction with the other embodiments. The locking pin 314 is aligned with a hinge 316. The hinge 316 connects the base 302 and the cap 320. The hinge 316 is, of course, preferably an integral or living hinge.

The cap 320 includes a cylinder 322 which extends upwardly from the hinge 316. Extending through the cylinder 322 is a slot 324. A hypodermic needle extends through the slot 324. The slot extends upwardly from the bottom of the cap 320.

A locking aperture 326 extends through the cylinder 322 adjacent to the hinge 316. The locking aperture 326 is appropriately dimensioned above the hinge 316 so that when the cap 320 is pivoted away from a needle, the locking aperture 326 will receive the locking pin 314 to secure the cap 320 away from the needle to allow the needle to be used. This is all as discussed above in conjunction with the other embodiments, and is similar to, if not substantially identical, to the illustrations of the locking pins and their apertures in securing the caps away from the needles.

The cylinder 322 is closed by a top wall 328.

In use, as may be understood from FIGS. 21, 22, and 23, the cap 320 may be disposed over a needle, and the base 302 is then wrapped about the barrel of the hypodermic syringe. The end 310 of the strap 304 extends through the aperture 306 and is pulled through the aperture 306. The serrations 312 extend outwardly, a slight distance greater than the height of the aperture 306. It will be noted that the edge serrations 312 include cam surfaces to provide for a general one-way extension or movement through the aperture 306. This is similar to a ratchet engagement. In this manner the base 302 is appropriately secured to the barrel of a hypodermic syringe.

With the shield apparatus 300 on a syringe, the unit is moved downwardly so that the tip of the needle is located well above the slot 324. The needle is accordingly protected by the shield apparatus 300. However, when it is desired to use the hypodermic syringe, the shield apparatus 300 is moved upwardly on the barrel until the tip of the needle is slightly below the top of the slot 324. Or, phrased in the alternative, the shield apparatus 300 is moved upwardly until the top of the slot 324 is slightly above the tip of the needle. The cap 320 is then pivoted on its hinge 316 until the locking pin 314 is disposed in the locking aperture 326. The needle is then exposed for use.

FIG. 18 is a perspective view of a portion of the shield apparatus 350. FIG. 19 is a view in partial section through the strap portion 354. FIG. 20 is a view in partial section taken generally along line 20—20 of FIG. 18. For the following discussion, reference will be made to all three of the FIGS. 18, 19, and 20.

FIGS. 18, 19, and 20 disclose another alternate embodiment of the shield apparatus of the present invention, namely shield apparatus 350. The shield apparatus 350 is essentially an alternate embodiment of the shield apparatus 300 in which the primary difference is in the configuration of the serrations which are used to secure the shield apparatus 350 to the barrel of a syringe. The shield apparatus 350 includes a base 352 and a cap 370. The base 352 includes a strap portion 354 and a locking portion 358. A locking aperture 356 extends through the strap portion 354 adjacent to an end of the strap portion remote from the locking portion 358. The locking portion 358 includes an end 360 remote from the strap portion 354. On the locking portion 358, and between the end 360 and the strap portion 354, are serrations 362. The serrations 362 extend into the strap portion 354 on the face of the strap portion 354, as opposed to the edge serrations 312 of the shield apparatus 300.

A hinge 366 connects the base 352 and the cap 370. Again, the hinge 366 is a living hinge, integral with the base 352 and the cap 370.

The cap 370 comprises a cylinder 372 through which extends a slot 374. A locking aperture 376 extends through the cylinder 374 adjacent the hinge 366. Again, the locking aperture 376 receives the locking pin 374 and the two elements are appropriately dimensioned with respect to the hinge 366 to allow for the pivoting or folding of the cap 370 away from the hypodermic needle to allow the cap to be locked during the use of the hypodermic syringe.

The cylinder 372 is, of course, closed by a cap, not shown.

The functioning of the shield apparatus 350 is substantially the same as that discussed above for the shield apparatus 300. The functioning or operation of the shield apparatus 350 may also be understood from reference to FIGS. 21, 22, and 23, all as substantially discussed above in conjunction with the apparatus 300.

FIG. 21 is a side view showing hypodermic syringe apparatus 400 with the shield apparatus 300, 350 in their safe, closed positions. FIG. 22 consecutively follows FIG. 21, showing the shield apparatus 300, 350 moved upwardly on the barrel 402, preparatory to the pivoting of the caps 320, 370. FIG. 23 consecutively follows FIG. 22, showing the needle 408 bared, ready for use with the hypodermic syringe 400, and the caps 320, 370 pivoted away from the needle 408 and locked in the open position of the shield apparatus.

FIGS. 21, 22, and 23 comprise side views illustrating the operation of the shield apparatus 300 and the shield apparatus 350 in conjunction with a hypodermic syringe 400. The hypodermic syringe 400 includes a barrel 402 and a needle 408. As discussed above, a shield apparatus is disposed about and secured to the barrel 402 and is moved downwardly to prevent the needle 408 from extending the slots 324 and 374. When use of the hypodermic syringe 400 is desired, the needle shields 300, 350 are moved upwardly until the top of the slots 324, 374 are slightly above the tip of the needle 408. The caps 320, 370 are then pivoted to allow the needle 408 to pass through slots 324, 374. The locking pins 314, 364 extend into the locking slots 326, 376 to keep the caps 320, 350 in locking position to allow the unrestricted use of the hypodermic syringe 400, with the needle 408 completely bared.

After the hypodermic syringe 400 has been used, then the caps 320, 350 are again moved or pivoted upwardly to disengage the locking pins 314, 364 from their locking slots 326, 376 and the needle 408 again passes through the slots 324, 374. The shield apparatus 300, 350 then move downwardly to the safe or closed position shown in FIG. 21. The syringe 400 with the shield apparatus 300, 350 secured thereto may then be safely disposed of with the needle 408 shielded to prevent an inadvertent contact or accidental injury.

FIG. 24 is a side view of a portion of an alternate cap embodiment 420 which may be used with hypodermic syringes having needles of different lengths. That is, a single cap may be used with hypodermic syringes having different lengths of needles. The cap accordingly may be considered as a generic cap.

The cap 420 includes a barrel 422 through which extends a slot 424. The length or height of the slot 424 may be varied by the simple expedient of having different cutout elements at the top or upper portion of the slot 424. Three slot elements 426, 428, and 430 are disposed above the slot 424. The outer peripheries of the slot elements 426, 428, and 430 are appropriately scored for easy removal of the slot elements.

The slot 424 may be of an appropriate length, minimum length, for the shortest needle which is typically found on a hypodermic syringe. For use with a hypodermic syringe having a slightly longer needle, or the next longest needle, the bottom slot element 426 may be easily broken away from the cylinder 422 by simple pressure on the slot element 426. The scored lines around the element 426 make for easy removal. After the slot element 426 is removed, the shield apparatus of which the cap 420 is a part may be appropriately secured to the hypodermic syringe barrel.

For use with an even longer needle, both the slots 426 and 428 may be removed. For the longest needle, all three of the slot elements 426, 428, and 430 may be removed.

It will be understood that the slot elements may have the height configured as desired, and there may be more than the three slot elements illustrated in FIG. 24, if desired, or if necessary. The idea is simply that a simple cylinder or cap, with an appropriate base, such as discussed above, may be used with hypodermic syringes regardless of the length of the needle of the syringe. Such a universal cap and shield apparatus has obvious advantages in that only a single mold will be required, as opposed to having a separate mold for each different needle size.

Moreover, the apparatus of the present invention may be configured and packaged with a needle to fit various sizes of syringe barrels. Such an embodiment is shown in FIGS. 25, 26, 27, 28 and 29.

Figures 25, 27, 28:
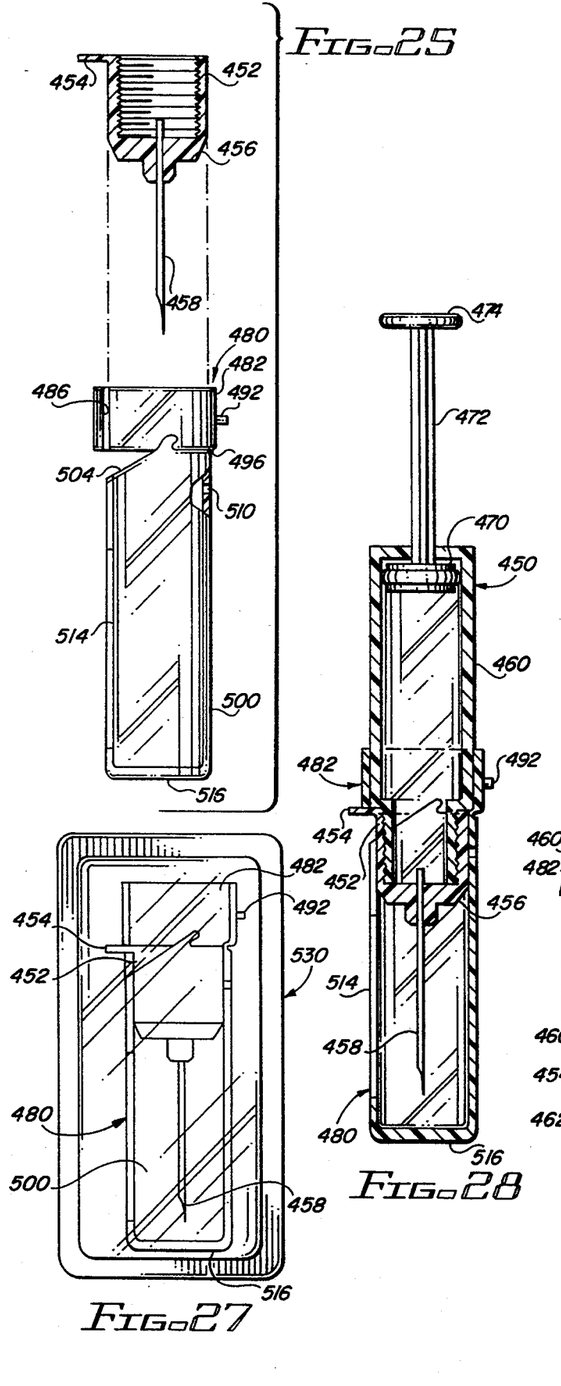
FIG. 25 is an exploded side view of another alternate embodiment of the apparatus of the present invention.
FIG. 27 is a side view of the apparatus of FIG. 25 as packaged for use.
FIG. 28 is a side view of the apparatus of FIG. 25 in its use environment.
Figure 26:
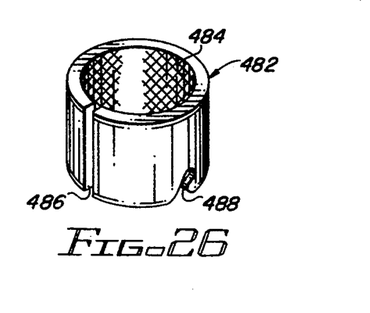
FIG. 26 is a perspective view of a portion of the apparatus of FIG. 25.

FIG. 25 is a side view of needle shield apparatus 480 spaced apart from a syringe base 452. A hypodermic needle 458 is secured to the syringe base 452. The needle shield apparatus 480 includes a slotted ring base 482 which is expandable to fit syringe barrels of various sizes and a slotted needle shield 500 secured to the base 482. FIG. 26 is a perspective view of the base 482.

FIG. 27 is a side view of the shield apparatus 480 packages with the syringe base 452.

Figure 29:
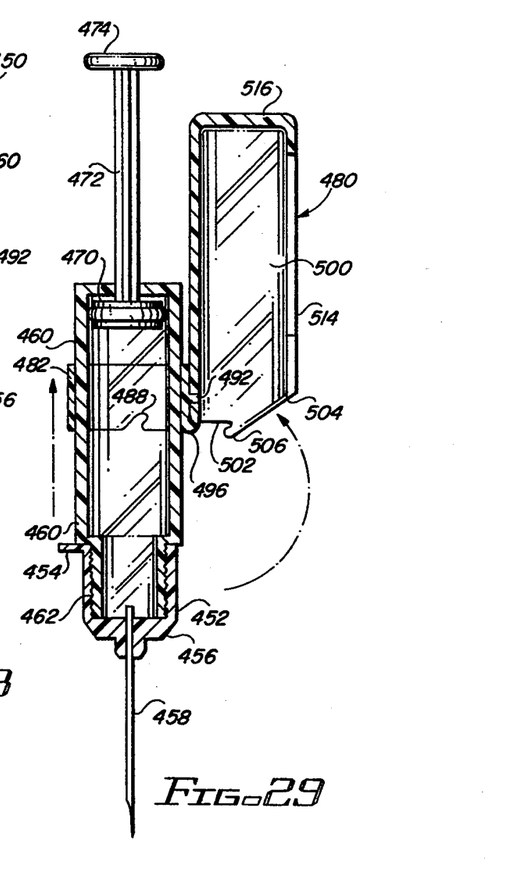
FIG. 29 is a side view sequentially following FIG. 28 illustrating the use of the apparatus.

FIG. 28 is a side view of the shield apparatus 480 disposed on syringe barrel and covering the needle 452. FIG. 29 is a side view of the apparatus of FIG. 28 sequentially following FIG. 28 with the needle shield 500 pivoted relative to the base 482 exposing the needle 458 for use.

For the following discussion, reference will generally be made to FIGS. 25, 26, 27, 28, and 29. Reference to a specific Figure will be made as appropriate.

In the embodiment of needle shield apparatus 480, a shield base ring or collar 482 is provided. The base ring or collar 482 is a generally cylindrical element with a longitudinally extending slot 486. The base ring or collar 482 includes an interior periphery 484, best shown in FIG. 26, that is knurled or otherwise includes frictional enhancements to help hold the shield apparatus 480 in place. The longitudinal slot 486, and the flexibility of the material out of which the base or collar 482 is made, allows the expansion of the base or collar so that the shield apparatus 480 will fit a relatively wide variety of syringe barrels of varying diameters.

Preferably, but not necessarily, the shield apparatus 480 will come pre-packaged with an internally threaded base 452 for a syringe, such as the syringe 450 shown in FIGS. 28 and 29. The base 452 is internally threaded so that it will mate with the external threads of a syringe barrel 460. The base 452 includes an outwardly extending lip 454 which act as the stop element to prevent the shield apparatus 480 from moving outwardly and away from the syringe. In other words, the lip 454 acts as a one way stop to prevent the shield apparatus from being removed from the base 452 and a needle 458 secured thereto.

The base 452 includes a tip portion 456 and the needle 458 extend through the tip portion 456 and upwardly, into the externally threaded barrel 460. This is shown in FIGS. 28 and 29.

In FIGS. 28 and 29, a piston or plunger is shown disposed within the barrel 460. A rod 472 is secured to the piston or plunger 470 and extends outwardly from the barrel 460. A thumb rest 474 is secured to the rod 472 externally of the barrel 460. Appropriate pressure on the thumb rest 474 results in the longitudinal movement of the piston 470 to expel the materials within the barrel 460 through the needle 458.

A pair of locking slots or recesses 488 extends through the base ring or collar 482. The locking slots or recesses include a locking slot or recess 488. A second locking slot or recess is disposed diametrically to the locking slot or recess 488.

A locking pin 492 extends outwardly from the base 482. The locking pin 492 cooperates with a recess in a shield 500 to secure the shield 500 to the base 482 for using the syringe apparatus 450.

The shield 500 is secured to the base 42 by a living hinge 496. The shield 500 includes a connecting rim 502 which abuts the base 482 when the shield 500 is in its operative position, as shown in FIGS. 25, 27, and 28. The shield 500 also includes a sloping rim 504 adjacent to the connecting rim 502.

Extending upwardly from the juncture of the connecting rim 502 and the sloping rim 504 are a pair of latches. The latch 506 is best shown in FIG. 25. The latch 506 is shown engaged in the locking slot 488 to secure the shield 500 to the base 482.

The shield 500, like the shields discussed above in the other embodiments, is a generally cylindrical element. It includes an end 516 remote from the connecting rim 502. An aperture 512 extends through the shield 500 for receiving the locking pin 492. The locking aperture 512 is aligned with the locking pin 492. This is best shown in FIG. 29.

A vertically extending needle slot 514 extends axially along the shield 500, downwardly from the lowest portion of the sloping rim 504. The purpose of the vertical needle slot 514 is, of course, to allow the shield 500 to move away from the needle 458. The needle 458 accordingly moves through the needle slot 514 to allow use of the syringe apparatus 450.

As shown in FIG. 29, the shield 500 pivots on its living hinge 496 through an arc of substantially 180 degrees. The locking pin 492 on the base 482 extends into the locking aperture 512 on the shield 500 to secure the shield 500 against the base 482. With the shield 500 away from the base 452, the tip 456, and the needle 458, the plunger 470 may be moved to discharge the material in the barrel 460 through the needle 458. However, in addition to the movement of the shield apparatus 480, or particularly of the shield 500 relative to the barrel 460, the entire shield apparatus 480 may be moved axially on the barrel 460. This is also shown in FIG. 29. The flexibility of the base 482 allow the base 482 to move on the barrel 460. The entire shield apparatus 480 may accordingly be moved away from the base 452. However, as indicated above, the lip 454 on the syringe base 452 limits the movement of the shield apparatus with respect to the base 452 in one direction. However, when the shield 500 is moved away from its closed or safety position, as shown in FIG. 28, to the position shown in FIG. 29, the shield apparatus 480 may then be moved to any desired location on the barrel 460.

Again referring the FIG. 27, the shield apparatus 480 is shown disposed on a syringe base 452 and the shield 500 is in position over the needle 458. The syringe base 452 and the shield apparatus 480 are disposed in a package 530. When the combination of the shield apparatus 480 and the syringe base 452 with the needle 458 are removed from the package 530, they are ready to be joined directly to a syringe barrel, such as the barrel 460. If the external threads on syringe barrels are relatively standardized, the actual dimension or length of the barrel 460 in immaterial with respect to the apparatus of the present invention. The longitudinal slot 486 of the base 482, together with the flexibility or pliability of the material out of which the base 482 is made, will allow the base 482 to fit a relatively wide range of barrel diameters.

At the same time, the relatively high coefficient of friction internal periphery 484 of the base 482 will allow the apparatus 480 to remain in place on the barrel 460. Positive movement on the apparatus 480, when the shield 500 is moved away from the needle 458, is required in order to move the base 482, and accordingly the entire apparatus 480, on the barrel 460.

In addition to moving longitudinally on a barrel, the base 482 may also be rotated on a barrel, as desired, so that the taper of the end of the needle 458 may be appropriately aligned, as desired.

In the embodiments of FIGS. 25–29, the diameter of the shield 500 is less than the diameter of the syringe barrel 460, and accordingly the shield cannot be moved axially along the barrel to expose the tip of the needle 458. Moreover, the lip 454 acts as a stop element to prevent the shield 480 from moving axially over the syringe barrel 460 to expose the tip of the needle 458.

It will also be noted that with the shield apparatus of the present invention, a needle may be readily reused, as in the administration of successive doses to the same patient.

It will be further noted that shield elements, including the needle shields and the outer cover elements have sometimes been referred to as "cylinders" or the like. The terms "cylinder", "cylindrical", and the like, are intended to include various configurations, and the terms are not limited to the pure mathematical definition. Similarly, the term "diameter" is intended to include the dimension corresponding to the configuration of the element to which the term pertains. Thus, to a square "cylinder", the term "diameter" comprises the width of the "cylinder", as appropriate.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What I claim is:

1. Needle safety shield apparatus for a syringe needle comprising in combination:
   base means to be secured to a syringe, including a locking pin,
   cylinder means pivotally secured to the base means for shielding the syringe needle, including
   a cylinder disposed over the needle and pivotable on the base means,
   a locking slot for receiving the locking pin when the cylinder is pivoted to expose the needle to lock the cylinder means to the base means,
   hinge means for pivoting the cylinder, and
   a slot in the cylinder aligned with the hinge means through which the needle extends when the cylinder means pivots on the base means to expose the needle;
   means for rotating the cylinder relative to the syringe and the needle to align the needle with the slot to allow the needle to pass through the slot to expose the needle; and means for securing the base means to the syringe.

2. The apparatus of claim 1 in which the cylinder means further includes a sheath disposed over the needle and secured to the base means, and the sheath includes a slot through which the needle passes when the cylinder means is pivoted on the base means to expose the needle.

3. The apparatus of claim 1 in which the base means further includes a fixed base secured to the syringe and an upper base pivotally movable on the fixed base.

4. The apparatus of claim 3 in which the cylinder means is secured to the upper base and the locking pin is secured to the fixed base.

5. The apparatus of claim 1 in which the base means further includes a fixed base secured to the syringe, and the cylinder means further includes a shield base movable relative to the fixed base, and the cylinder is pivotally secured to the shield base.

6. The apparatus of claim 5 in which the locking pin is secured to the shield base.

7. The apparatus of claim 5 in which the fixed base includes a first groove and a second groove, and the shield base includes a ridge which is disposed in the first groove when the cylinder means is shielding the syringe needle and the shield base is movable to the second groove preparatory to pivoting the cylinder means to expose the syringe needle.

8. The apparatus of claim 5 in which the cylinder means further includes means for pivoting the cylinder means relative to the fixed base.

9. The apparatus of claim 8 in which the means for pivoting the cylinder means relative the fixed base includes a pivot tab secured to the shield base.

10. The apparatus of claim 1 in which the means for securing the base means to the syringe comprises a strap secured to the base means.

11. The apparatus of claim 1 in which the base means is movable on the syringe for moving the cylinder away from the needle after the cylinder is pivoted away from the needle.

12. Hypodermic syringe and shield apparatus comprising in combination:
    a syringe having a first diameter;
    a needle secured to the syringe;
    shield means secured to the syringe and disposed over the needle for shielding the needle, including
    a needle shield secured to the syringe having a second diameter which is less than the first diameter of the syringe for preventing the needle shield from moving axially along the syringe,
    hinge means for pivoting the needle shield relative to the syringe and the needle, and
    a slot in the needle shield through which the needle moves as the needle shield pivots to expose the needle for use; and an outer shield disposed over the needle shield.

13. The apparatus of claim 12 in which the shield means further includes a base securable to the syringe, and the hinge means for pivoting the needle shield is secured to the base.

14. The apparatus of claim 12 in which the outer shield is disposed on the needle shield and is rotatable thereon.

15. The apparatus of claim 14 in which the outer shield includes a slot to be aligned with the slot in the needle shield when the needle shield is pivoted to expose the needle.

16. The apparatus of claim 13 in which the base is movable axially on the syringe to allow the needle shield to pivot to expose the needle.

17. Hypodermic syringe and shield apparatus comprising in combination:
    a hypodermic syringe;
    a hypodermic needle secured to the hypodermic syringe; and
    shield means for shielding the hypodermic needle, including
    a base secured to the hypodermic syringe,
    a needle shield rotatably and pivotally secured to the base, and
    a slot in the needle shield aligned with the needle by rotating the needle shield and through which the hypodermic needle moves as the needle shield is pivoted.

18. The apparatus of claim 17 in which the base is movable axially on the hypodermic syringe in order to allow the needle shield to be pivoted to expose the hypodermic needle.

* * * * *